(12) United States Patent
Videcoq et al.

(10) Patent No.: US 9,743,833 B2
(45) Date of Patent: Aug. 29, 2017

(54) METHOD AND DEVICE FOR ACQUIRING AND COMPUTING DATA FROM AN OPHTHALMIC OBJECT

(71) Applicant: Luneau Technology Operations, Pont de l'Arche (FR)

(72) Inventors: Jean-Jacques Videcoq, Pavilly (FR); Michaël Vassard, Boos (FR)

(73) Assignee: LUNEAU TECHNOLOGY OPERATIONS, Pont de l'Arche (FR)

( * ) Notice: Subject to any disclaimer, the term of this patent is extended or adjusted under 35 U.S.C. 154(b) by 186 days.

(21) Appl. No.: 14/523,030

(22) Filed: Oct. 24, 2014

(65) Prior Publication Data

US 2015/0116474 A1    Apr. 30, 2015

(51) Int. Cl.
*A61B 3/14* (2006.01)
*G05B 19/12* (2006.01)
(Continued)

(52) U.S. Cl.
CPC .............. *A61B 3/145* (2013.01); *G02C 7/024* (2013.01); *G05B 19/128* (2013.01);
(Continued)

(58) Field of Classification Search
CPC ...... A61B 3/145; G02C 7/024; G05B 19/128; G05B 19/4207
(Continued)

(56) References Cited

U.S. PATENT DOCUMENTS 5,604,583 A    2/1997 Byron et al.
6,837,580 B2   1/2005 Senda et al.
(Continued)

FOREIGN PATENT DOCUMENTS

FR    2854268 A1    10/2004
FR    2959831 A1    11/2011

OTHER PUBLICATIONS

Search Report and Written Opinion by The National Industrial Property Institute (INPI) on Aug. 20, 2014.

*Primary Examiner* — William C Vaughn, Jr.
*Assistant Examiner* — Jae N Noh
(74) *Attorney, Agent, or Firm* — Michael B. Fein; Eckert Seamans Cherin & Mellott, LLC

(57) ABSTRACT

This method, which allows acquisition and computation of geometrical data of at least one pattern associated with an ophthalmic object (6) for manufacturing ophthalmic lenses similar to the object or complementary thereto, is of the type in which a device (12) for acquiring and computing geometrical data is used, which comprises:

a transparent support (13) adapted for bearing an ophthalmic object;
on one side of the support, means (17) for illuminating this support;
on the other side of the support, a video camera (25) adapted for producing a video signal representative of at least one pattern associated with the ophthalmic object laid on the support; and
signal processing and analysis means (27) receiving at the input the video signal produced by the camera, and adapted for computing and providing the geometrical data.

The method is characterized in that:
(a) a verification pattern independent of said geometrical data is traced on the ophthalmic object (6), this verification pattern being asymmetrical relatively to each of two axes perpendicular to each other;
(b) the ophthalmic object is positioned on the transparent support (13) of the acquisition and display device (12); and
(c) by means of said device (12), said verification pattern is optically captured and analyzed.

18 Claims, 3 Drawing Sheets

(51) Int. Cl.
*G05B 19/42* (2006.01)
*G02C 7/02* (2006.01)
(52) U.S. Cl.
CPC .............. *G05B 19/4207* (2013.01); *G05B 2219/34342* (2013.01); *G05B 2219/37129* (2013.01); *G05B 2219/42222* (2013.01); *G05B 2219/45175* (2013.01); *Y02P 90/10* (2015.11)
(58) Field of Classification Search
USPC .......................................................... 348/78
See application file for complete search history.

(56) References Cited

U.S. PATENT DOCUMENTS

| | | | |
|---|---|---|---|
| 2007/0291258 A1* | 12/2007 | Divo | .................. G01M 11/0235 356/124 |
| 2010/0321635 A1* | 12/2010 | Apter | .................... G02C 7/028 351/159.75 |
| 2013/0075465 A1 | 3/2013 | Schneider | |

* cited by examiner

METHOD AND DEVICE FOR ACQUIRING AND COMPUTING DATA FROM AN OPHTHALMIC OBJECT

CROSS-REFERENCE TO RELATED APPLICATIONS

The application claims the benefit of French Patent Application Serial No. 1360446, filed Oct. 25, 2013, which is hereby incorporated by reference.

The present invention relates to a method for acquiring and computing geometrical data of at least one pattern associated with an ophthalmic object, such as a presentation lens, an ophthalmic lens or a template, for manufacturing ophthalmic lenses similar to the object or complementary thereto, the method being of the type in which a device is used for acquiring and computing geometrical data, said device comprising:
  a transparent support adapted for bearing an ophthalmic object;
  on one side of the support, means for illuminating this support;
  on the other side of the support, a video camera oriented towards the support and adapted for producing a video signal representative of at least one pattern associated with the ophthalmic object laid on the support; and
  signal processing and analyzing means receiving at the input the video signal produced by the camera, and adapted so as to compute and provide geometrical data intended for making the lens.

A presentation lens is a non-corrective lens in transparent plastic material, having the contour and optionally at least one borehole, similar to those of an ophthalmic lens (or glass) to be made. A template is a planar object having the same shape as the lens to be reproduced. It may be provided with boreholes to be reproduced.

A geometrical pattern will generally designate the contour of the object, or marking lines notably locating the geometrical axis of the orientation of an ophthalmic lens, but it may also designate attachment boreholes formed in the presentation lens, in a lens or in a template representing a finished lens. Other marking lines may form patterns, notably lines for marking the centre of the pupil of a user.

In the methods above, the patterns are always patterns used for making lenses, i.e. for driving a machining machine, notably a machine for grinding lenses from a circular blank.

In particular, FR-A-2 854 268 describes a method of the aforementioned type giving the possibility of accurately positioning an adaptor on an optical glass blank and obtaining data used for driving a grinding and/or drilling machine for ophthalmic lenses with numerical control.

In every case, the ophthalmic object to be analyzed should be positioned on the transparent support in a predetermined position, as regards both the face of the object which is facing the support and its orientation in its general plane. An error on the actual lens or on its positioning leads to scrapping of the lens.

The object of the invention is to allow easy and reliable consideration of the actually used ophthalmic object as well as its positioning on the support.

For this purpose, the object of the invention is a method of the aforementioned type, characterized in that:
  (a) a verification pattern independent of said geometrical data is traced on the ophthalmic object, this verification pattern being asymmetrical relatively to each of two axes perpendicular to each other;
  (b) the ophthalmic object is positioned on the transparent support of the acquisition and display device; and
  (c) by means of said device, said verification pattern is optically captured and analyzed.

According to embodiments of this method:
  from the analysis of said verification pattern, the computations to be made on said geometrical data are determined;
  the device includes a monitor comprising a screen, and the glasses of the spectacle frame with automatic replacement of the lenses at their respective right or left positions, and with reorientation of each lens relatively to a frame axis associated with the spectacle frame are displayed on the screen of the monitor;
  an alert depending on the nature of the ophthalmic object, on the face of the object directed towards the screen and/or on the orientation of this object around an axis perpendicular to the support is further displayed on the screen of the monitor;
  said device contains pieces of information representative of standard images of said verification pattern for each of the ophthalmic objects and for each of the possible positioning modes of these ophthalmic objects, and step (c) is carried out by means of said device in the following way:
    (c1) correcting the orientation of the image of the ophthalmic object.
    (c2) optically recognizing said captured verification pattern; and
    (c3) comparing the captured verification pattern with said standard images
  in step (a), an indication representative of a characteristic of the frame, notably the measurement of the bridge, is also traced on the object, and this indication is recognized by optical read out and used by said device for computing data intended for making the lens, Correspondingly, the object of the invention is also a device for acquiring and displaying geometrical data of at least one pattern associated with an ophthalmic object, such as a presentation lens, a lens or a template, for making ophthalmic lenses similar to the object or complementary thereto, of the type comprising:
  a transparent support adapted for bearing an ophthalmic object;
  on one side of the support, means for illuminating this support;
  on the other side of the support, a video camera oriented towards the support and adapted for producing a video signal representative of at least one pattern associated with the ophthalmic object laid on the support; and
  signal analysis and processing means receiving as input the video signal produced by the camera, and adapted for computing and providing geometrical data intended for making the lens;
  the device being characterized in that it comprises means for optical recognition and analysis of the actual image of a verification pattern independent of said geometrical data borne by the ophthalmic object positioned on the transparent support, this verification pattern being asymmetrical relatively to each of two axes perpendicular to each other.

According to embodiments of this device:
  it comprises means for determining the computations to be made on said geometrical data from the analysis of said verification pattern;
  it comprises a monitor including a screen and means for displaying on the screen the lenses of the frame while having automatically replaced the lenses in their respective right or left positions, and having reoriented each lens relatively to the frame axis associated with the frame;

it comprises means for displaying on the screen an alert depending on the ophthalmic object, on the face of this object directed towards the screen and/or on the orientation of this object around an axis perpendicular to the support;

said display means include means for displaying a window in which are indicated the nature of the object, said face and/or said orientation;

it comprises means for storing representative pieces of information of standard images, for at least one ophthalmic object, of an asymmetrical verification pattern relatively to each of two axes perpendicular to each other, these standard images corresponding to each ophthalmic object and to the different possible positionings of this ophthalmic object on the support with a predetermined orientation of the ophthalmic object, means for correcting the orientation of the image of the ophthalmic object laid on the support, and means for comparing said actual image and said standard images.

Exemplary embodiments of the invention will now be described with reference to the appended drawings, wherein:

FIG. 1 schematically illustrates from the front, a spectacle frame provided with two presentation lenses adapted for applying the method according to the invention;

FIG. 2 schematically illustrates an acquisition and display device according to the invention;

FIG. 3 schematically illustrates a portion of the device of FIG. 2;

Figure 2:
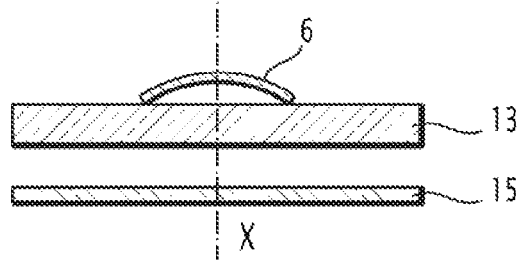
Figure 2:
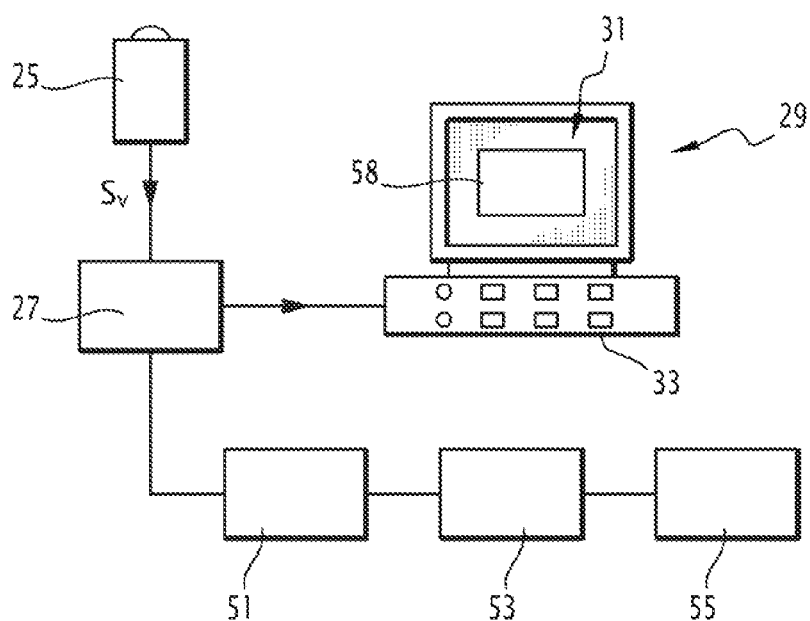
Figure 9:
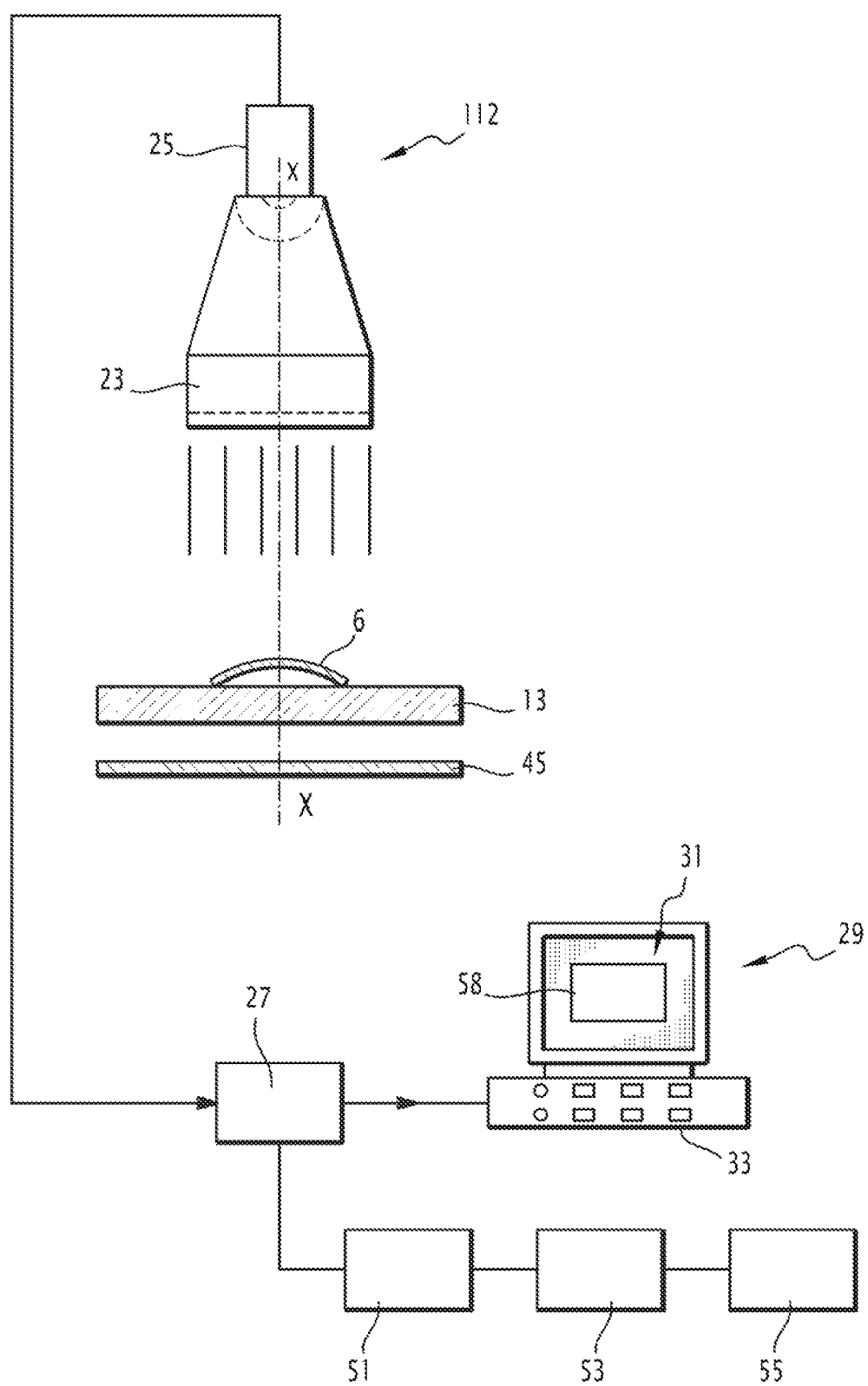

FIG. 9 schematically illustrates an alternative of the device of FIG. 2.

Figure 1:
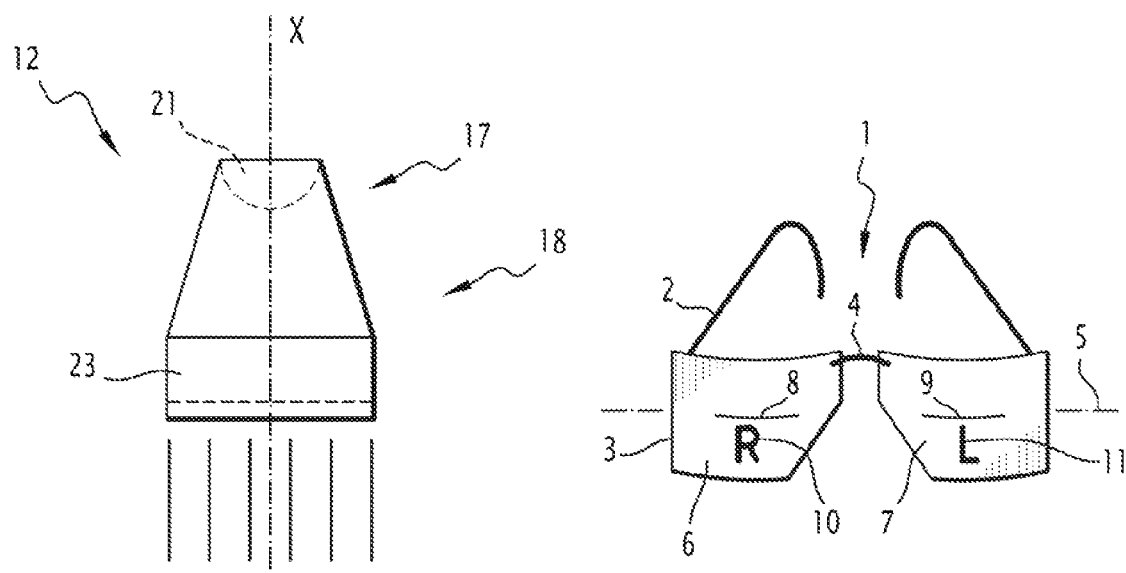

A spectacle frame 1 is illustrated in FIG. 1, which comprises two branches 2 and two frame rings 3 connected through a bridge 4. With this frame 1 is associated a frame axis 5 parallel to the tangent to both rings 3 at the top of the latter. The frame is supposed to be symmetrical relatively to a vertical middle plane.

The frame 1 is equipped with two right 6 and left 7 transparent and non-corrective presentation lenses, the shape of which has to be reproduced accurately from an optical glass blank in order to form a pair of spectacles.

Each lens 6, 7 bears on one of its faces, a line 8, 9 which extends along the frame axis 5. For this reason, the line 8, 9 is designated by the expression <<axis for mounting the lens>>.

Each lens 6, 7 further has a respective verification pattern 10, 11 which is independent of the optical and geometrical data used for driving the machining, for example grinding, machine. Each verification pattern 10, 11 is specific to the lens 6 or 7. Further it is asymmetrical relatively to any straight line parallel to the frame axis 5 and relatively to any straight line perpendicular to this axis. Preferably, each verification pattern 10, 11 is chiral, i.e., it does not have any axis of symmetry comprised in its plane.

In the illustrated example, the verification pattern 10 of the right presentation lens 6 is formed by the letter R, while the verification pattern 11 of the left presentation lens 7 is formed by the letter L.

Both of these verification patterns are traced by hand on the convex face (front face) of both lenses 6, 7, substantially parallel to the line 8, 9.

In FIG. 2, an acquisition, measurement and display device 12 according to the invention is illustrated schematically, which may notably essentially be such as described in the aforementioned FR-A-2 854 268, with a similar analysis and calculation mode.

This device comprises a transparent, planar and horizontal, glass plate 13, forming a support for the ophthalmic object to be analyzed. The latter is here formed by the right presentation lens 6, which rests through its peripheral edges on the upper planar surface of the glass plate 13. The lens 6 therefore has its concave face turned towards the support 13. Under the supporting plate 13 a planar projection screen 15 is positioned in parallel, which may notably consist of a ground glass plate or a sheet of translucent material, of the tracing paper type. Means 17 for illuminating the object are positioned above the supporting plate 13, so as to illuminate the whole of the object 6 and to project a shadow of the object on the projection screen 15, through the supporting plate 13. These illumination means 17 essentially consist of a light source 21, for example a LED, and of an optical assembly or collimator 23, in general formed by a set of lenses. Each set 23 is intended to channel the light radiation emitted by the source and to ensure regular illumination of the object 6 with vertical light rays.

The image of the object 6 formed on the projection screen 15, this image being in fact a shadow of the object on the screen 15, is observed with an array video camera 25 connected to a signal processing and image analysis unit 27, itself connected to a monitor 29. The monitor 29 comprises a display screen 31 and a pad 33 for controlling and adjusting the display.

The image analysis unit 27 includes an input connected to the output of the camera 25 in order to receive the video signal S, produced by the camera, and an output connected to the monitor 29 in a way described later on.

Figure 3:
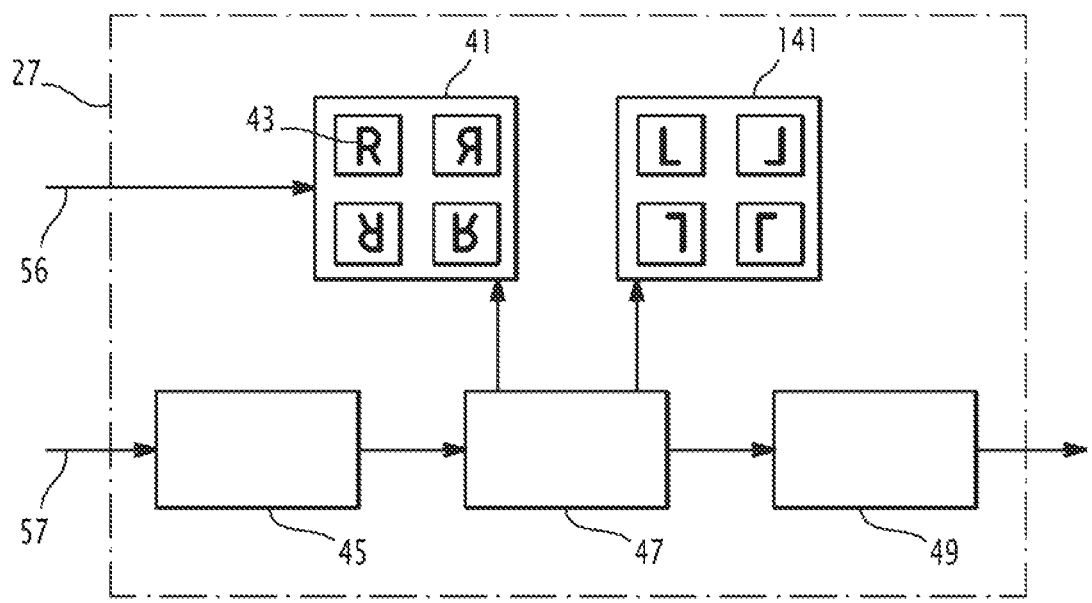

As schematized in FIG. 3, the unit 27 includes a memory 41 containing the standard images 43 of the pattern 10 in the four possible cases of positioning of the lens 6 on the support 13, illustrated in FIGS. 4 to 7:

concave face and right position (FIG. 4) layout,
concave face and inverted position (FIG. 5) layout,
convex face and right position (FIG. 6) layout,
convex face and inverted position (FIG. 7) layout.

The expressions of <<right position>> and <<inverted position>> define the orientation of the lens 6 around a vertical axis, i.e. perpendicular to the support 13.

These positions are understood with the frame axis positioned horizontally.

The unit 27 also includes a device 45 for optically recognizing characters, a comparator 47 connected to the device 45 and to the memory 43, and a device 49 connected to the comparator 47.

Of course, the unit 27 includes a second memory 141 similar to the memory 41 and relative to the pattern 11. The comparator 47 is also connected to this second memory.

The device further comprises programming means 51 connected to the analysis and processing unit 27 on the one hand and to a unit 53 for controlling the grinding machine 55 on the other hand.

As described in the aforementioned FR-A-2 854 268, the analysis and processing unit 27 may comprise means for image correction in order to take into account the distortion of the pixels depending on the distance to the vertical central axis X-X of the camera 25 and of the illumination means 21.

In every case it comprises means for correcting the orientation of the frame axis 8, 9 borne by the object laid on the support 13.

In the following, only the portion of the analysis and display method relating to the verification pattern 10 or 11 will be described, it being understood that the analysis and the display of the contour of the lens 6, 7 and of the frame axis 8, 9 which it bears, are carried out in a conventional way, for example as described in the aforementioned FR-A.

The operator lays one of the two lenses on the support 13, with its frame axis substantially horizontal.

The image of the lens is first of all straightened or <<re-centered>> so that the frame axis 8, 9 is horizontal. For this, the image processing unit 27 identifies the frame axis 8, 9 and operates a rotation of the image so that this frame axis is horizontal. This re-centering of the frame is described in the aforementioned FR-A.

Next the image of the lens captured by the camera 25 is transmitted to the device 45 through a line 57 indicated in FIG. 3. The image of the verification pattern, localized in the image by the device 45, is compared in 47 with the standard images from the memories 41 and 141 and identified.

Thus, the device 12 recognizes whether this is the right or left lens, and how it is positioned. It adapts itself its computations to the lens 6 or 7 present on the support, and to the positioning of the latter, in order to generate the required geometrical data for the grinding machine.

Figure 4:
FIGS. 4 to 7 illustrate diverse images of a presentation lens of the frame of FIG. 1, as displayed on the screen of the device of FIG. 2, depending on the positioning of this lens on the support of the device.
Figure 5:
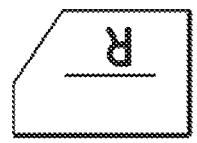
Figure 6:
Figure 7:
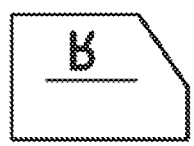

Thus:

if one is in the configuration of FIG. 6, the inversion of the verification pattern along a vertical axis gives the possibility of determining whether the right lens has been laid on its convex face in a right position, and the device associated with this position with the contour of the lens, for the continuation of the processing.

if one is in the configuration of FIG. 7, by inverting the pattern along both horizontal and vertical axes, it is possible to determine that the right lens was laid on its convex face, but the lens is turned by 180° relatively to the position which it has in the frame. The processing unit automatically produces a rotation of 180° of the contour and associates with the obtained contour the convex face of the lens;

if one is in the configuration of FIG. 4 or 5, the non-inversion or inversion along the vertical axis gives the possibility of determining whether the lens was laid on its concave face. As this configuration may lead to inaccuracies on the measurement of the contour, depending on the curvature and the shape of the lens, a message may, in an alternative, be sent to the user, via the device 49 and the screen 31, in order to inform him/her. The operator may then either continue the processing in this configuration, or again start the capturing of the image after having placed the lens on its convex face.

Further, the device 49 causes display on the screen 31 of a window 58 (FIG. 2) in which both lenses of the frame are drawn while displaying the right lens and the left lens at their respective places.

For this, the contour of the lens has been re-centered beforehand relatively to the frame axis 8, 9. For this purpose, the image processing unit 27 identifies the frame axis 8, 9 and performs a rotation of the image so that this frame axis is horizontal. This re-centering of the frame is described in the aforementioned FR-A.

As this is understood, the verification pattern 10, 11 is analyzed at the same time and in the same way as the contour and the line 8, and optionally as other patterns borne by the presentation lens and used for the grinding.

Optionally, the verification pattern may be completed with a substantially horizontal handwritten indication representative of the size of the bridge 4 of the frame, and/or with another datum used for making ophthalmic lenses. The unit 27 is then adapted for recognizing this datum and for displaying it on the screen 31 and/or by taking it into account without the operator needing to enter it manually.

Figure 8:
FIG. 8 is an alternative of FIG. 6.

Thus, in the example illustrated in FIG. 8, the letter R is associated with the number 19, representative of the width (in mm) of the bridge 4.

This optionally allows the operator to carry out an additional verification.

The acquisition and display device 112 illustrated in FIG. 9 only differs from the device 12 of FIG. 2 by interchanging the position of the illumination means and of the camera 25.

Indeed, the illumination means are formed by a planar and horizontal diffuser 45 positioned under the support 13, in the place of the screen 15 of FIG. 2, while the camera 25 is positioned above the collimator 23, by looking downwards along the axis X-X. In this case, it is the image of the object laid on the support 13 which is captured by the camera, and no longer its shadow on a screen as this was the case with the device of FIG. 2.

The device 112 may be used in a similar way to the device 12 for carrying out the verification of the nature (either right or left) and of the positioning of the presentation lens used. Of course, the verification images are then right or left inverted for each of the four positioning situations.

In every case, the geometrical data computed by the device 12 or 112 are used for positioning a mounting adaptor on a blank of the lens to be made on the one hand, and then for driving the grinding machine 55. The first of these steps, a so-called blocking step, may be carried out in the device 12 or 112, or in a separate blocking device to which the computed data are provided.

The invention claimed is:

1. A method for acquiring and computing geometrical data of at least one pattern associated with an ophthalmic object, such as a presentation lens, an ophthalmic lens or a template for manufacturing ophthalmic lenses similar to the object or complementary thereto, wherein a device for acquiring and computing geometrical data is used, said device comprising:

a transparent support adapted for bearing an ophthalmic object;

on one side of the support, means for illuminating this support:

on the other side of the support, a video camera oriented towards the support and adapted for producing a video signal representative of at least one pattern associated with the ophthalmic object laid on the support; and signal processing and analysis means receiving as input the video signal produced by the camera, and adapted so as to compute and provide geometrical data intended for making the lens, and wherein:

(a) a verification pattern independent of said geometrical data is traced on the ophthalmic object, this verification pattern being chiral, wherein the verification pattern has no symmetry around any axis;

(b) the ophthalmic object is positioned on the transparent support of the acquisition and display device;

(c) by means of said device, said verification pattern is optically captured and analyzed; and (d) from the analysis of the verification pattern, the face of the ophthalmic object on which rests the ophthalmic object positioned on the support is determined.

2. The method according to claim 1, wherein from the analysis of said verification pattern, the computations to be carried out on said geometrical data are determined.

3. The method according to claim 1, wherein at the device includes a monitor including a screen, and in that the lenses of the frame are displayed on the screen of the monitor, by having automatically replaced the lenses in their respective right or left positions, and by having re-oriented each lens relatively to a frame axis associated with the frame.

4. The method according to claim 3, wherein an alert depending on the nature of the ophthalmic object, on the face of the object directed towards the screen and/or on the orientation of this object around an axis perpendicular to the support is further displayed on the screen of the monitor.

5. The method according to claim 1, wherein said device contains information representative of standard images of said verification pattern for each of the ophthalmic objects and for each of the possible positioning modes of these ophthalmic objects, and in that step (c) is carried out by means of the device in the following way:
 (c1) correcting the orientation of the image of the ophthalmic object;
 (c2) optically recognizing said captured verification pattern; and
 (c3) comparing the captured verification pattern with said standard images.

6. The method according to claim 1, wherein in step (a), an indication representative of a characteristic of a frame, notably the measurement of the bridge, is also traced on the object, and in that this indication is recognized by optical read out and is used by said device for computing the data intended for making the lens.

7. A device for acquiring and displaying geometrical data of at least one pattern associated with an ophthalmic object, such as a presentation lens, a lens or a template, for manufacturing ophthalmic lenses similar to the object or complementary thereto, of the type comprising:
 a transparent support adapted for bearing an ophthalmic object;
 on one side of the support, means for illuminating this support;
 on the other side of the support, a video camera oriented towards the support and adapted for producing a video signal representative of at least one pattern associated with the ophthalmic object laid on the support; and
 signal processing and analysis means receiving as input the video signal produced by the camera, and adapted for computing and providing geometrical data intended for making the lens;
wherein the device comprises means for optically recognizing and analyzing the actual image of a verification pattern independently of said geometrical data borne by the ophthalmic object positioned on the transparent support, this verification pattern being chiral, wherein the verification pattern has no symmetry around any axis, and
means for determining, from the analysis of the actual image of said verification pattern, the face of the ophthalmic object on which rests the ophthalmic object positioned on the support.

8. The device according to claim 7, comprising means for determining the computations to be made on said geometrical data from the analysis of said verification pattern.

9. The device according to claim 8, comprising:
 a monitor including a screen; and
 means for displaying on the screen the lenses of the frame by having automatically replaced the lenses in their respective right or left positions, and having reoriented each lens relatively to a frame axis associated with the frame.

10. The device according to claim 9, comprising means for displaying on the screen an alert depending on the ophthalmic object, on the face of this object directed towards the screen and/or on the orientation of this object around an axis perpendicular to the support.

11. The device according to claim 10, wherein said display means include means for displaying a window in which are indicated the nature of the object, of said face and/or of said orientation.

12. The device according to claim 7, comprising:
 means for storing representative information of standard images, for at least one ophthalmic object, of a verification pattern asymmetrical relatively to each of two axes perpendicular to each other, these standard images corresponding to each ophthalmic object and to the different possible positionings of this ophthalmic object on the support with a predetermined orientation of the ophthalmic object;
 means for correcting the orientation of the image of the ophthalmic object laid on the support; and
 means for comparing said actual image and said standard images.

13. The method according to claim 2, wherein the device includes a monitor including a screen, and in that the lenses of the frame are displayed on the screen of the monitor, by having automatically replaced the lenses in their respective right or left positions, and by having re-oriented each lens relatively to a frame axis associated with the frame.

14. The method according to claim 2, wherein said device contains information representative of standard images of said verification pattern for each of the ophthalmic objects and for each of the possible positioning modes of these ophthalmic objects, and in that step (c) is carried out by means of the device in the following way:
 (c1) correcting the orientation of the image of the ophthalmic object;
 (c2) optically recognizing said captured verification pattern; and
 (c3) comparing the captured verification pattern with said standard images.

15. The method according to claim 3, wherein said device contains information representative of standard images of said verification pattern for each of the ophthalmic objects and for each of the possible positioning modes of these ophthalmic objects, and in that step (c) is carried out by means of the device in the following way:
 (c1) correcting the orientation of the image of the ophthalmic object;
 (c2) optically recognizing said captured verification pattern; and
 (c3) comparing the captured verification pattern with said standard images.

16. The method according to claim 4, wherein said device contains information representative of standard images of said verification pattern for each of the ophthalmic objects and for each of the possible positioning modes of these ophthalmic objects, and in that step (c) is carried out by means of the device in the following way:
 (c1) correcting the orientation of the image of the ophthalmic object;
 (c2) optically recognizing said captured verification pattern; and (c3) comparing the captured verification pattern with said standard images.

17. The method according to claim 2, wherein in step (a), an indication representative of a characteristic of a frame, notably the measurement of the bridge, is also traced on the object, and in that this indication is recognized by optical read out and is used by said device for computing the data intended for making the lens.

18. The method according to claim 3, wherein in step (a), an indication representative of a characteristic of a frame, notably the measurement of the bridge, is also traced on the object, and in that this indication is recognized by optical read out and is used by said device for computing the data intended for making the lens.

* * * * *